United States Patent
Lee et al.

(10) Patent No.: US 7,483,746 B2
(45) Date of Patent: Jan. 27, 2009

(54) STIMULATION OF THE STOMACH IN RESPONSE TO SENSED PARAMETERS TO TREAT OBESITY

(75) Inventors: Philip H. J. Lee, Santa Clarita, CA (US); Todd K. Whitehurst, Santa Clarita, CA (US); Carla M. Woods, Beverly Hills, CA (US)

(73) Assignee: Boston Scientific Neuromodulation Corp., Valencia, CA (US)

( * ) Notice: Subject to any disclaimer, the term of this patent is extended or adjusted under 35 U.S.C. 154(b) by 421 days.

(21) Appl. No.: 11/295,783

(22) Filed: Dec. 6, 2005

(65) Prior Publication Data

US 2006/0129201 A1 Jun. 15, 2006

Related U.S. Application Data

(60) Provisional application No. 60/633,830, filed on Dec. 6, 2004.

(51) Int. Cl.
*A61N 1/00* (2006.01)
(52) U.S. Cl. .......................................... 607/40
(58) Field of Classification Search ............ 607/40, 607/41, 133
See application file for complete search history.

(56) References Cited

U.S. PATENT DOCUMENTS

| | | | |
|---|---|---|---|
| 3,760,984 A | 9/1973 | Theeuwes | |
| 3,845,770 A | 11/1974 | Theeuwes et al. | |
| 3,916,899 A | 11/1975 | Theeuwes et al. | |
| 3,923,426 A | 12/1975 | Theeuwes | |
| 3,987,790 A | 10/1976 | Eckenhoff et al. | |
| 3,995,631 A | 12/1976 | Higuchi et al. | |
| 4,016,880 A | 4/1977 | Theeuwes et al. | |
| 4,036,228 A | 7/1977 | Theeuwes | |
| 4,111,202 A | 9/1978 | Theeuwes | |
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |
| 4,327,725 A | 5/1982 | Cortese et al. | |
| 4,360,019 A | 11/1982 | Portner et al. | |
| 4,487,603 A | 12/1984 | Harris | |

(Continued)

FOREIGN PATENT DOCUMENTS

WO WO 01/82398 A1 11/2001
WO WO 03/005465 A1 1/2003

OTHER PUBLICATIONS

Daniel John DiLorenzo, Method and Apparatus for Neuromodulation and Phsyiologic Modulation for the treatment of Metabolic and Neuropsychiatric Disease, Jun. 21, 2004, 67 pages.

*Primary Examiner*—George Manuel
(74) *Attorney, Agent, or Firm*—AdvantEdge Law Group, LLC

(57) ABSTRACT

Systems for treating an obese patient include one or more sensors configured to sense one or more physical parameters of the patient and one or more implanted stimulators configured to apply a stimulus to the stomach in response to the sensed parameters. Methods of treating an obese patient include sensing one or more physical parameters of the patient and applying a stimulus to the stomach with one or more implanted stimulators in response to the sensed parameters.

17 Claims, 12 Drawing Sheets

U.S. PATENT DOCUMENTS

| | | | |
|---|---|---|---|
| 4,562,751 A | 1/1986 | Nason et al. | |
| 4,627,850 A | 12/1986 | Deters et al. | |
| 4,678,408 A | 7/1987 | Nason et al. | |
| 4,685,903 A | 8/1987 | Cable et al. | |
| 4,692,147 A | 9/1987 | Duggan | |
| 4,725,852 A | 2/1988 | Gamblin et al. | |
| 4,865,845 A | 9/1989 | Eckenhoff et al. | |
| 5,057,318 A | 10/1991 | Magruder et al. | |
| 5,059,423 A | 10/1991 | Magruder et al. | |
| 5,080,653 A | 1/1992 | Voss et al. | |
| 5,097,122 A | 3/1992 | Colman et al. | |
| 5,112,614 A | 5/1992 | Magruder et al. | |
| 5,137,727 A | 8/1992 | Eckenhoff | |
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,312,439 A | 5/1994 | Loeb | |
| 5,501,703 A | 3/1996 | Holsheimer et al. | |
| 5,728,396 A | 3/1998 | Peery et al. | |
| 6,051,017 A | 4/2000 | Loeb et al. | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,280,873 B1 | 8/2001 | Tsukamoto | |
| 6,368,315 B1 | 4/2002 | Gillis et al. | |
| 6,381,496 B1 | 4/2002 | Meadows et al. | |
| 6,458,171 B1 | 10/2002 | Tsukamoto | |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,591,137 B1 * | 7/2003 | Fischell et al. | 607/40 |
| 6,611,715 B1 * | 8/2003 | Boveja | 607/40 |
| 6,620,151 B2 | 9/2003 | Blischak et al. | |
| 6,666,845 B2 | 12/2003 | Hooper et al. | |
| 6,740,072 B2 | 5/2004 | Starkweather et al. | |
| 6,760,626 B1 | 7/2004 | Boveja | |
| 6,770,067 B2 | 8/2004 | Lorenzen et al. | |
| 6,826,428 B1 * | 11/2004 | Chen et al. | 607/40 |
| 2001/0046625 A1 | 11/2001 | Ruth, II et al. | |
| 2001/0053476 A1 | 12/2001 | Ruth et al. | |
| 2002/0161414 A1 * | 10/2002 | Flesler et al. | 607/40 |
| 2003/0009202 A1 * | 1/2003 | Levine | 607/58 |
| 2003/0018367 A1 * | 1/2003 | DiLorenzo | 607/46 |
| 2003/0120321 A1 * | 6/2003 | Bumm | 607/40 |
| 2003/0144708 A1 * | 7/2003 | Starkebaum | 607/40 |
| 2004/0015201 A1 * | 1/2004 | Greenstein | 607/40 |
| 2004/0059393 A1 * | 3/2004 | Policker et al. | 607/40 |
| 2005/0021104 A1 | 1/2005 | DiLorenzo | |
| 2005/0149142 A1 * | 7/2005 | Starkebaum | 607/40 |
| 2006/0167498 A1 | 7/2006 | DiLorenzo | |

* cited by examiner

STIMULATION OF THE STOMACH IN RESPONSE TO SENSED PARAMETERS TO TREAT OBESITY

RELATED APPLICATIONS

The present application claims the priority under 35 U.S.C. § 119(e) of previous U.S. Provisional Patent Application No. 60/633,830, filed Dec. 6, 2004, which is incorporated herein by reference in its entirety.

BACKGROUND

Obesity is one of the most prevalent public heath problems in the United States and affects millions of Americans. An especially severe type of obesity, called morbid obesity, is characterized by a body mass index greater than or equal to 40 or a body weight that is 100 pounds over normal weight.

Recent studies have shown that over 300,000 deaths are caused by obesity in the United States each year. In addition, millions suffer broken bones, social isolation, arthritis, sleep apnea, asphyxiation, heart attacks, diabetes, and other medical conditions that are caused or exacerbated by obesity.

Patients suffering from obesity have very limited treatment options. For example, drugs such as sibutramine, diethylproprion, mazindol, phentermine, phenylpropanolamine, and orlistat are often used to treat obesity. However, these drugs are effective only for short-term use and have many adverse side-effects.

Another treatment option for obesity is surgery. For example, a procedure known as "stomach stapling" reduces the effective size of the stomach and the length of the nutrient-absorbing small intestine to treat obesity. However, surgery is highly invasive and is often associated with both acute and chronic complications including, but not limited to, infection, digestive problems, and deficiency in essential nutrients.

SUMMARY

Systems for treating an obese patient include one or more sensors configured to sense one or more physical parameters of the patient and one or more implanted stimulators configured to apply a stimulus to the stomach in response to the sensed parameters.

Methods of treating an obese patient include sensing one or more physical parameters of the patient and applying a stimulus to the stomach with one or more implanted stimulators in response to the sensed parameters.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Systems and methods for treating an obese patient are described herein. One or more sensors are configured to sense one or more physical parameters of the patient. The physical parameters may include, but are not limited to, stomach distension, stomach strain, an electrical signal produced by the stomach, a rate of digestion of food within the stomach, food intake into the stomach, one or more gastric slow waves produced by the stomach, or any other obesity factor. One or more implanted stimulators are configured to apply a stimulus to the stomach in response to the sensed parameters.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1A:
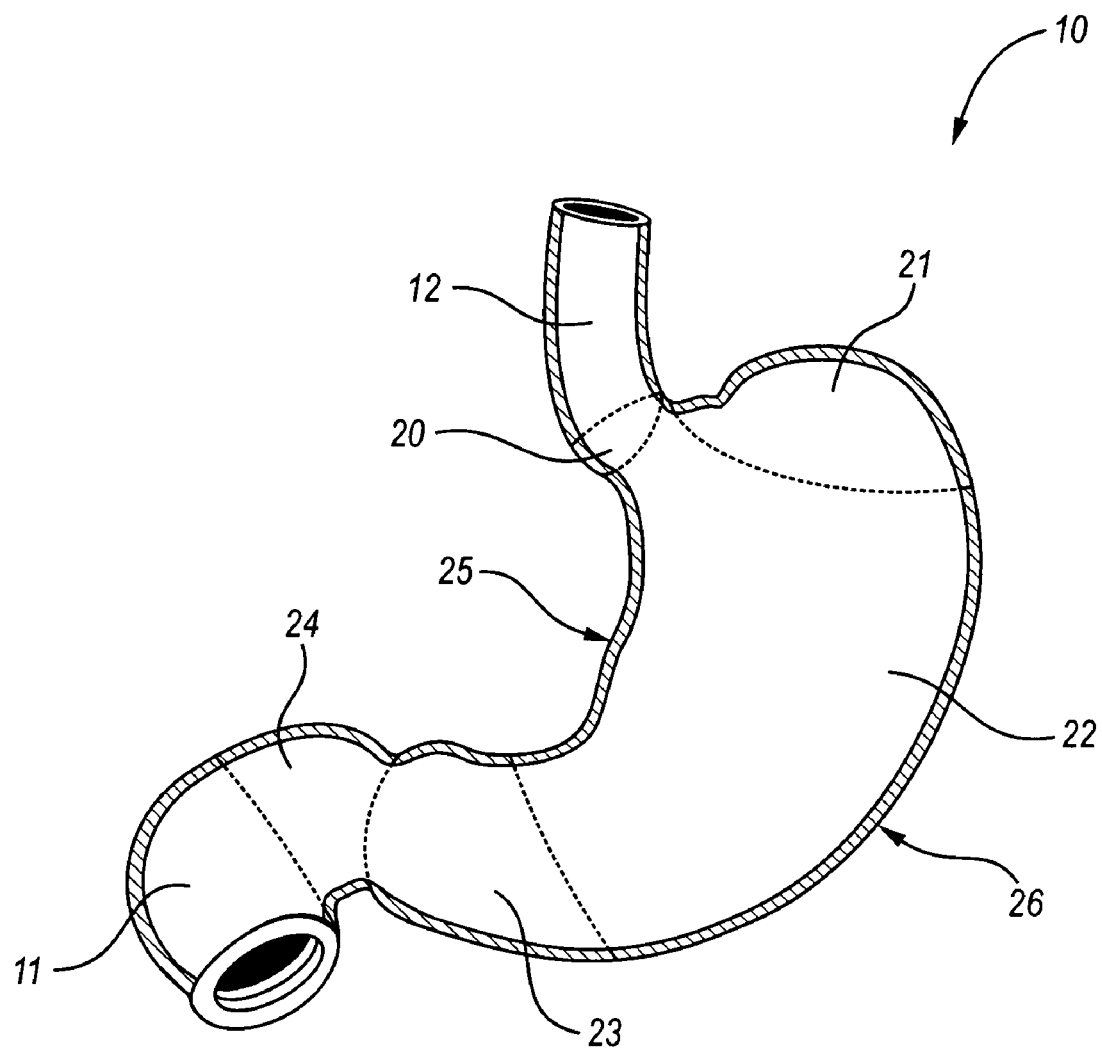
FIG. 1A is an exemplary diagram of the stomach.

FIG. 1A is an exemplary diagram of a stomach (10). As shown in FIG. 1A, the shape of the stomach (10) as viewed from the side has two curves, the lesser curvature (25) and the greater curvature (26), which respectively follow the upper and lower surfaces of the stomach (10). The cardia or proximal stomach (20) is located in the upper left portion of the stomach (10) and serves as the junction between the esophagus (12) and the body (22) of the stomach (10). The fundus (21), which is also located in the upper portion of the stomach (10), produces acid and pepsin that help digest food. The lower portion of the stomach (10) is known as the distal stomach and includes the antrum (23) and pylorus (24). The antrum (23) is where food is mixed with gastric juice. The pylorus (24) acts as a valve to control emptying of the stomach contents into the small intestine (11).

The stomach (10) has five nested layers of tissue. The innermost layer is where stomach acid and digestive enzymes are made and is called the mucosa. A supporting layer, know as the submucosa, surrounds the mucosa. The mucosa and submucosa are surrounded by a layer of muscle, known as the muscularis, that moves and mixes the stomach contents. The next two layers, the subserosa and the outermost serosa, act as wrapping layers for the stomach (10).

Figure 1B:
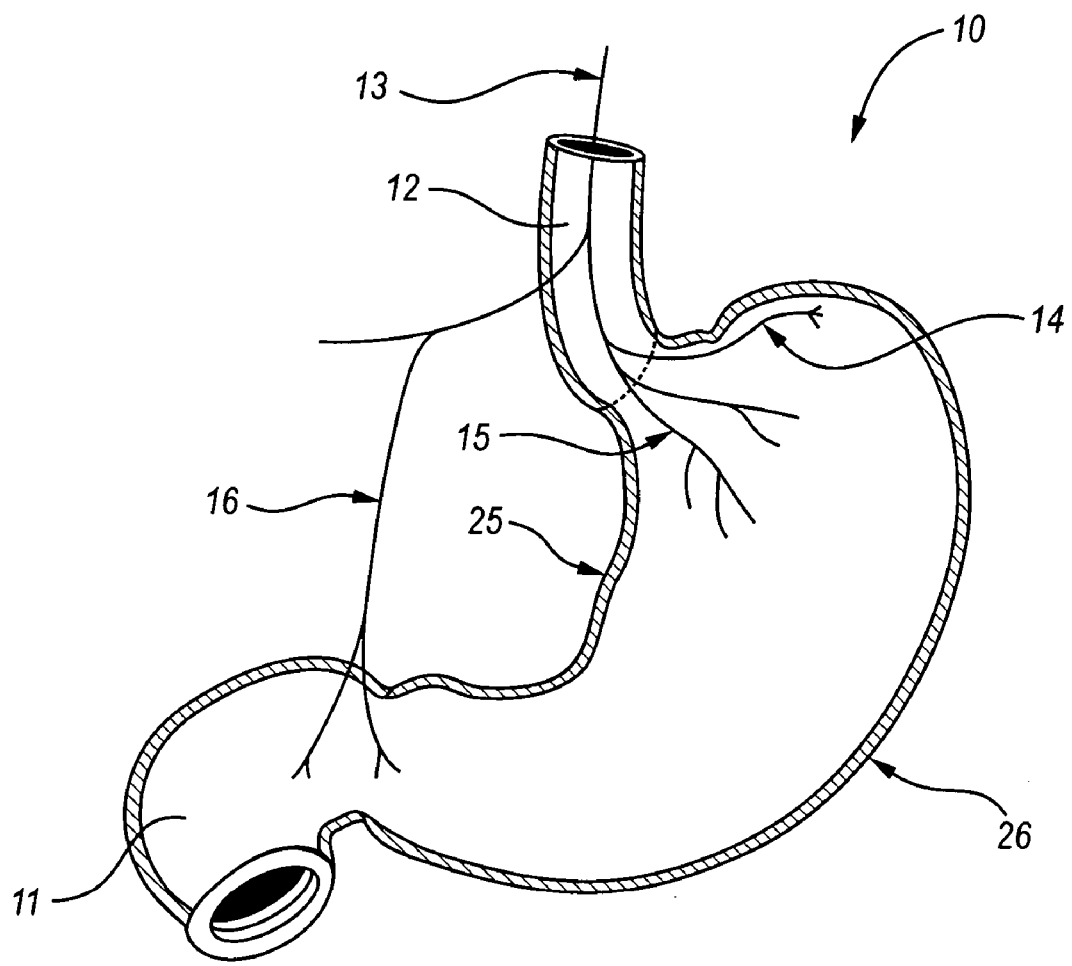
FIG. 1B shows various branches of the anterior vagal trunk that innervate the stomach.

Innervation of the stomach (10) is provided directly by the vagi nerves and through subsidiary plexuses of the celiac plexus. FIG. 1B shows various branches of the anterior vagal trunk (13), which is derived from the left vagus nerve. The hepatic branch (14) runs through the upper part of the lesser omentum and joins the plexus on the hepatic artery and portal vein. The celiac branch (15) follows the left gastric artery to the celiac plexus. The gastric branch (16), the largest of the three, follows the lesser curvature (25) of the stomach (10) and distributes anterior gastric branches to the distal portions of the stomach (10), i.e., those portions of the stomach (10) adjacent the entrance to the small intestine (11).

Figure 1C:
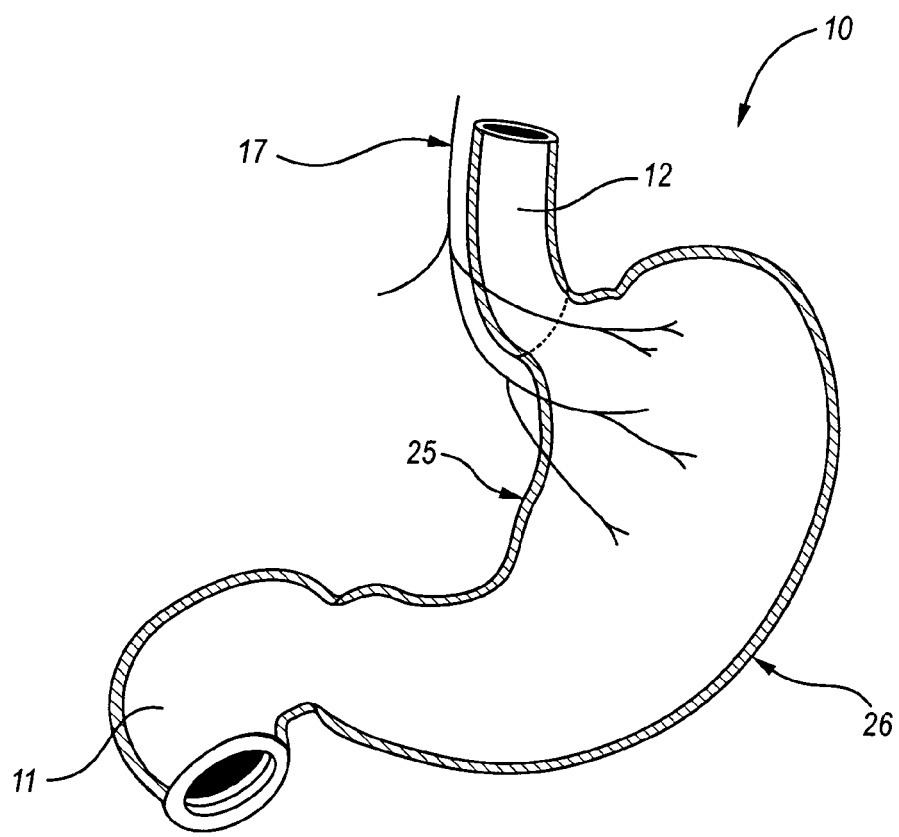
FIG. 1C shows various branches of the posterior vagal trunk that innervate the stomach.

FIG. 1C shows various branches of the posterior vagal trunk (17), which innervates the posterior surface of the stomach (10). The posterior vagal trunk (17) is derived largely, but not entirely from the right vagus nerve.

Both sympathetic efferent and afferent nerves to the stomach (10) are derived from T6-T9 spinal cord segments. These nerve fibers are transmitted by the greater thoracic splanchnic nerve. Preganglionic fibers relay in the celiac ganglia and the nerves reach the stomach (10) along the branches of the celiac artery.

As used herein and in the appended claims, the term "food" will be used to refer generally to any type of nutrient bearing substance in whatever form, e.g., food and/or drink, that enters the stomach (10). Food that is input into the stomach (10) enters through the esophagus (12), passes through the stomach (10) and exits at the distal end of the stomach (10) into the small intestine (11). A typical stomach (10) generates electrical pulses which signal to the neurological system of a person that the stomach is full and that the person should stop eating.

The stomach (10) is emptied as a result of coordinated gastric contractions (motility). Without these coordinated contractions, digestion and absorption of dietary nutrients cannot take place. Thus, impairment of gastric contractions may result in delayed emptying of the stomach (10).

Gastric contractions are regulated by myoelectrical activity of the stomach (10), called slow waves. Gastric slow waves originate in the proximal portion of the stomach (10), e.g., near the esophagus (12), and propagate distally toward the small intestine (11). Gastric slow waves determine the maximum frequency, propagation velocity, and propagation direction of gastric contractions. The normal frequency of the gastric slow waves is about three cycles per minute (cpm) in humans. Abnormalities in gastric slow waves lead to gastric motor disorders and have been frequently observed in patients with functional disorders of the stomach, such as gastroparesis, functional dyspepsia, anorexia, etc. Some studies have shown that patients with obesity have an abnormally rapid rate of gastric slow waves.

As will be explained in more detail below, an obese patient may be treated by applying a stimulus to the stomach. In some examples, the stimulus may cause the patient to feel a sensation of fullness which helps the patient limit food intake. A stimulus may also be applied to slow an abnormally rapid rate of gastric slow waves causing the stomach of an obese patient to process food at a more normal rate and again help the patient limit food intake. The stimulus may be applied to any portion of the stomach as best suits a particular patient or particular condition. For example, the stimulus may be applied to one or more walls of the stomach, one or more nerves that innervate the stomach, one or more blood vessels that supply the stomach, or any other tissue within the stomach. Consequently, a stimulator may be implanted in a patient to deliver a stimulus to the stomach to treat obesity. The present specification will describe methods and systems for implanting such a stimulator to most conveniently treat obesity.

As used herein, and in the appended claims, the term "stimulator" will be used broadly to refer to any device that delivers a stimulus, such as an electrical stimulation current, one or more drugs or other chemical stimulation, thermal stimulation, electromagnetic stimulation, mechanical stimulation, and/or any other suitable stimulation to the stomach. Thus, the term "stimulator" includes, but is not limited to, a stimulator, microstimulator, implantable pulse generator (IPG), system control unit, or similar device. As used herein and the appended claims, any reference to stimulating the stomach will encompass stimulating any selected portion of the stomach, including, but not limited to a wall of the stomach, a nerve that innervate the stomach, a blood vessel that supplies the stomach, or any other tissue within the stomach.

Figure 2:
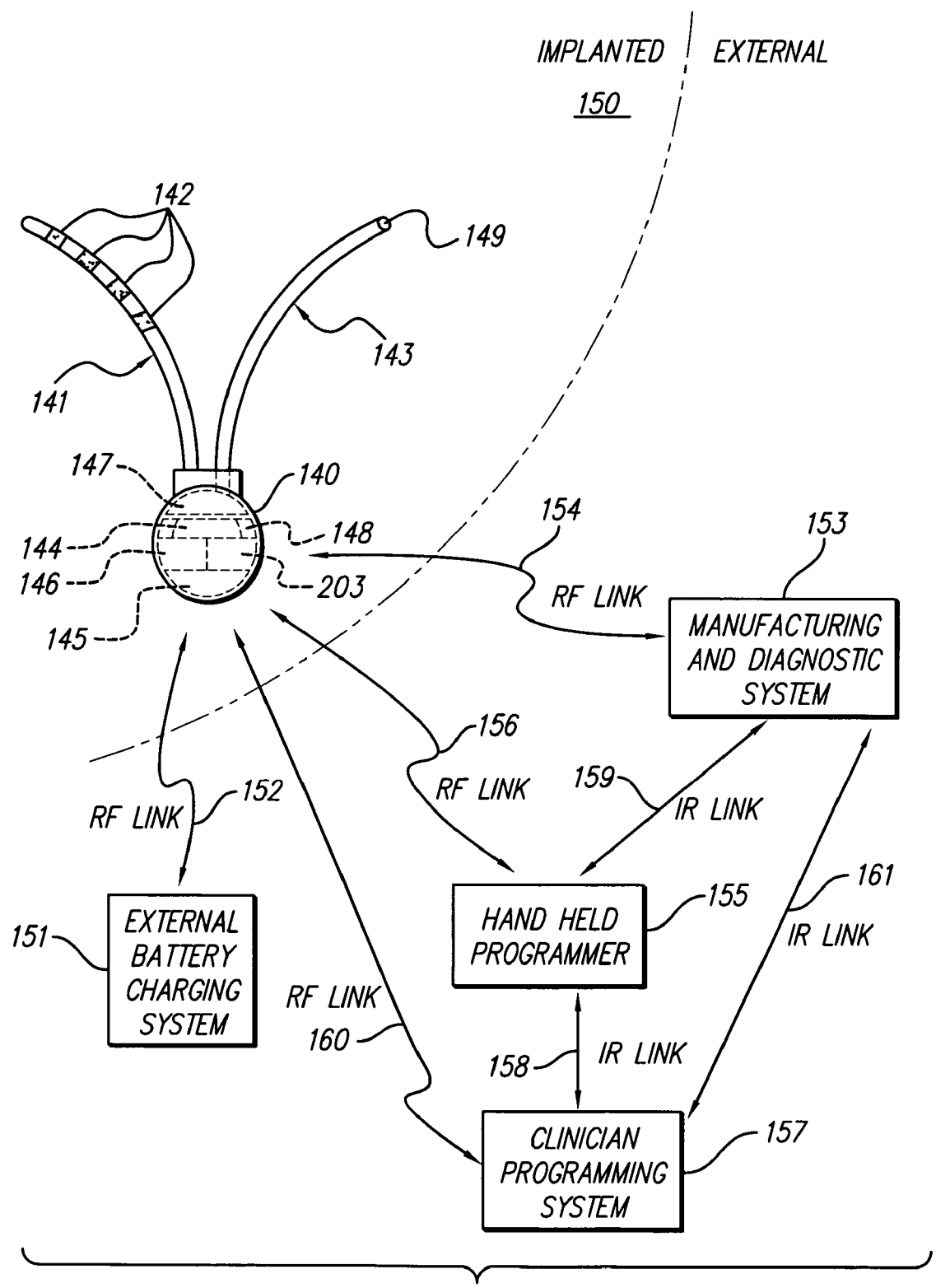
FIG. 2 illustrates an exemplary stimulator that may be used to apply a stimulus to the stomach according to principles described herein.

To facilitate an understanding of the methods of stimulating the stomach with an implanted stimulator, a more detailed description of the stimulator and its operation will now be given with reference to the figures. FIG. 2 illustrates an exemplary stimulator (140) that may be implanted within a patient (150) and used to apply a stimulus to the stomach, e.g., an electrical stimulation of the stomach, an infusion of one or more drugs at the stomach, or both. The electrical stimulation function of the stimulator (140) will be described first, followed by an explanation of the possible drug delivery function of the stimulator (140). It will be understood, however, that the stimulator (140) may be configured to provide only electrical stimulation, only a drug stimulation, both types of stimulation, or any other type of stimulation as best suits a particular patient.

The exemplary stimulator (140) shown in FIG. 2 is configured to provide electrical stimulation to the stomach and may include a lead (141) having a proximal end coupled to the body of the stimulator (140). The lead (141) also includes a number of electrodes (142) configured to apply an electrical stimulation current to the stomach. The lead (141) may include any number of electrodes (142) as best serves a particular application. The electrodes (142) may be arranged as an array, for example, having at least two or at least four collinear electrodes. In some embodiments, the electrodes (142) are alternatively inductively coupled to the stimulator (140). The lead (141) may be thin (e.g., less than 3 millimeters in diameter) such that the lead (141) may be positioned near the stomach. In some alternative examples, as will be illustrated in connection with FIG. 3, the stimulator (140) is leadless.

As illustrated in FIG. 2, the stimulator (140) includes a number of components. It will be recognized that the stimulator (140) may include additional and/or alternative components as best serves a particular application. A power source (145) is configured to output voltage used to supply the various components within the stimulator (140) with power and/or to generate the power used for electrical stimulation. The power source (145) may be a primary battery, a rechargeable battery, a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link. One type of rechargeable battery that may be used is described in International Publication WO 01/82398 A1, published Nov. 1, 2001, and/or WO 03/005465 A1, published Jan. 16, 2003, both of which are incorporated herein by reference in their respective entireties. Other battery construction techniques that may be used to make a power source (145) include those shown, e.g., in U.S. Pat. Nos. 6,280,873; 6,458,171, and U.S. Publications 2001/0046625 A1 and 2001/0053476 A1, all of which are incorporated herein by reference in their respective entireties. Recharging can be performed using an external charger.

The stimulator (140) may also include a coil (148) configured to receive and/or emit a magnetic field (also referred to as a radio frequency (RF) field) that is used to communicate with, or receive power from, one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs at the stomach to treat obesity.

Additionally, if multiple external devices are used in the treatment of a patient, there may be some communication among those external devices, as well as with the implanted stimulator (140). Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stomach via the electrodes (142). In some embodiments, the stimulator (140) may be configured to produce monopolar stimulation. The stimulator (140) may alternatively or additionally be configured to produce multipolar stimulation including, but not limited to, bipolar or tripolar stimulation.

The electrical circuitry (144) may include one or more processors configured to decode stimulation parameters and generate the stimulation pulses. In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (140) to adjust the stimulation parameters such that the stimulation applied by the stimulator (140) is safe and efficacious for treatment of a particular patient. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation or vice versa. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to the stomach including, but not limited to, the frequency, pulse width, amplitude, electrode polarity configuration (i.e., anode-cathode assignment), burst pattern (e.g., burst on time and burst off time), duty cycle or burst repeat interval, ramp on time, and ramp off time of the stimulation current that is applied to the stomach. The drug stimulation parameters may control various parameters including, but not limited to, the amount of drugs infused at the stomach, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different patients and/or types of obesity. Thus, in some embodiments, the stimulation parameters may be adjusted by the patient, a clinician, or other user of the stimulator (140) as best serves a particular patient. The stimulation parameters may also be automatically adjusted by the stimulator (140), as will be described below. For example, the amplitude of the stimulus current applied to a nerve that innervates the stomach may be adjusted to have a relatively low value so as to target relatively large diameter fibers of the nerve. The stimulator (140) may also increase excitement of nerves in the stomach by applying a stimulation current having a relatively low frequency (e.g., less than 100 Hz) to the stomach. The stimulator (140) may also decrease excitement of nerves in the stomach by applying a relatively high frequency (e.g., greater than 100 Hz) to the stomach. The stimulator (140) may also be programmed to apply the stimulation current to the stomach intermittently or continuously. Different stimuli may be applied to determine which will help a particular patient feel a sensation of fullness or help the patient's stomach process food at a normal rate so as to help the patient limit the intake of unnecessary calories contributing to the obesity.

Additionally, the exemplary stimulator (140) shown in FIG. 2 is configured to provide drug stimulation to a patient by applying one or more drugs to the stomach. For this purpose, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs at the stomach. In some embodiments, the stimulator (140) may include multiple catheters (143) and/or pumps (147) for storing and infusing dosages of the one or more drugs at the stomach.

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

The one or more drugs applied by the stimulator (140) may include any drug or other substance configured to treat obesity. For example, the drugs may include, but are not limited to, peptides, cholecystokinin (CCK), peptide YY (PYY), Urocortin, corticotrophin-releasing factors (CRF), sibutramine, diethylproprion, mazindol, phentermine, phenylpropanolamine, and orlistat. The one or more drugs may additionally or alternatively include, but are not limited to, medications, anesthetic agents, synthetic or natural peptides or hormones, neurotransmitters, cytokines, and other intracellular and intercellular chemicals.

The one or more drugs may also include excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)). The one or more drugs may also include inhibitory neurotransmitters (e.g., dopamine, glycine, and gamma-aminobutyric acid (GABA)), agonists thereof, and agents that act to increase levels of an inhibitory neurotransmitter(s) (e.g., benzodiasepine (e.g., chlordiazepoxide, clonazepam, diazepam, lorazepam, oxazepam, prazepam alprazolam); flurazepam, temazepam, or triazolam).

The stimulator (140) may also include a sensor device (203) configured to sense any of a number of indicators related to stomach activity, digestion, or any other factor related to obesity. For example, the sensor (203) may include a pressure sensor or transducer, a strain gauge, a force transducer, or some other device configured to sense stomach distension that occurs as a result of food intake. In some examples, the sensor (203) may be located on the lead (141). The sensor (203) may alternatively be a separate device configured to communicate with the stimulator (140). The sensor (203) will be described in more detail below.

The stimulator (140) of FIG. 2 is illustrative of many types of stimulators that may be used to stimulate the stomach to treat obesity. For example, the stimulator (140) may include an implantable pulse generator (IPG) coupled to one or more leads having a number of electrodes, a spinal cord stimulator (SCS), a drug pump (mentioned previously), a micro-drug pump (mentioned previously), or any other type of implantable stimulator configured to deliver a stimulus to the stomach. Exemplary IPGs suitable for use as described herein include, but are not limited to, those disclosed in U.S. Pat. Nos. 6,381,496, 6,553,263; and 6,760,626. Exemplary spinal cord stimulators suitable for use as described herein include, but are not limited to, those disclosed in U.S. Pat. Nos. 5,501,703; 6,487,446; and 6,516,227. All of these listed patents are incorporated herein by reference in their respective entireties.

Alternatively, the stimulator (140) may include an implantable microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017 and U.S. patent application Ser. No. 11/285,983 entitled "Affixation Member for Implantable Stimulators" to Whitehurst, et al., filed Nov. 23, 2005. All of these listed patents and application are incorporated herein by reference in their respective entireties.

Figure 3:
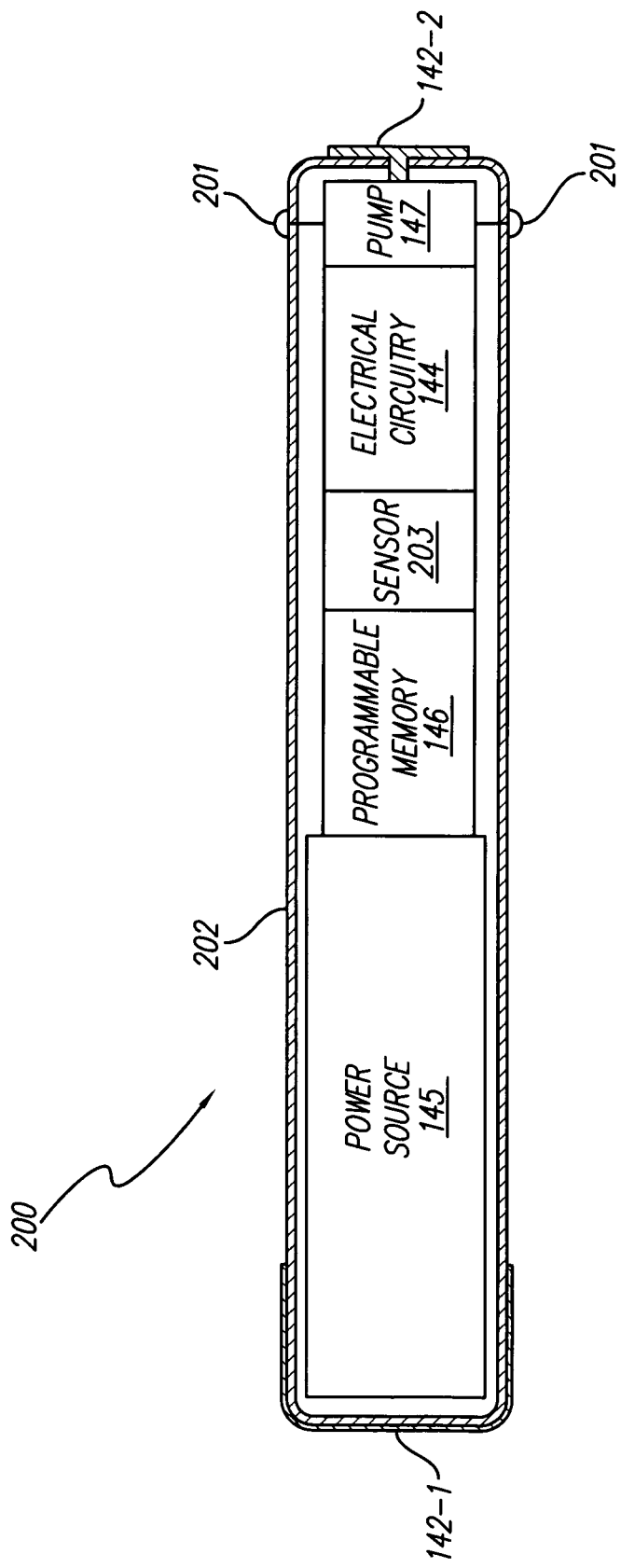
FIG. 3 illustrates an exemplary microstimulator that may be used as the stimulator according to principles described herein.

FIG. 3 illustrates an exemplary microstimulator (200) that may be used as the stimulator (140; FIG. 2) described herein. Other configurations of the microstimulator (200) are possible, as shown in the above-referenced patents and as described further below.

As shown in FIG. 3, the microstimulator (200) may include the power source (145), programmable memory (146), electrical circuitry (144), sensor (203), and pump (147) described in connection with FIG. 2. These components are housed within a capsule or housing (202). The capsule (202) may be a thin, elongated cylinder or any other shape as best serves a particular application. The shape of the capsule (202) may be determined by the structure of the desired target nerve, the surrounding area, and the method of implantation. In some embodiments, the capsule (202) is substantially equal to or less than three cubic centimeters.

In some embodiments, the microstimulator (200) may include two or more leadless electrodes (142). Either or both of the electrodes (142) may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of the microstimulator (200), while allowing most elements of the microstimulator (200) to be located in a more surgically convenient site. This minimizes the distance traversed and the surgical planes crossed by the microstimulator (200) and any lead(s).

The external surfaces of the microstimulator (200) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator (200) may also include one or more infusion outlets (201). The infusion outlets (201) facilitate the infusion of one or more drugs at the stomach to treat obesity. The infusion outlets (201) may dispense one or more drugs directly to the treatment site. Alternatively, as will be described in more detail below, catheters may be coupled to the infusion outlets (201) to deliver the drug therapy to a treatment site some distance from the body of the microstimulator (200). The stimulator (200) of FIG. 3 also includes electrodes (142-1 and 142-2) at either end of the capsule (202). One of the electrodes (142) may be designated as a stimulating electrode to be placed close to the treatment site and one of the electrodes (142) may be designated as an indifferent electrode used to complete a stimulation circuit.

The microstimulator (200) may be implanted within a patient with a surgical tool such as a hypodermic needle, bore needle, or any other tool specially designed for the purpose. Alternatively, the microstimulator (200) may be implanted using endoscopic or laparoscopic techniques.

Figure 4:
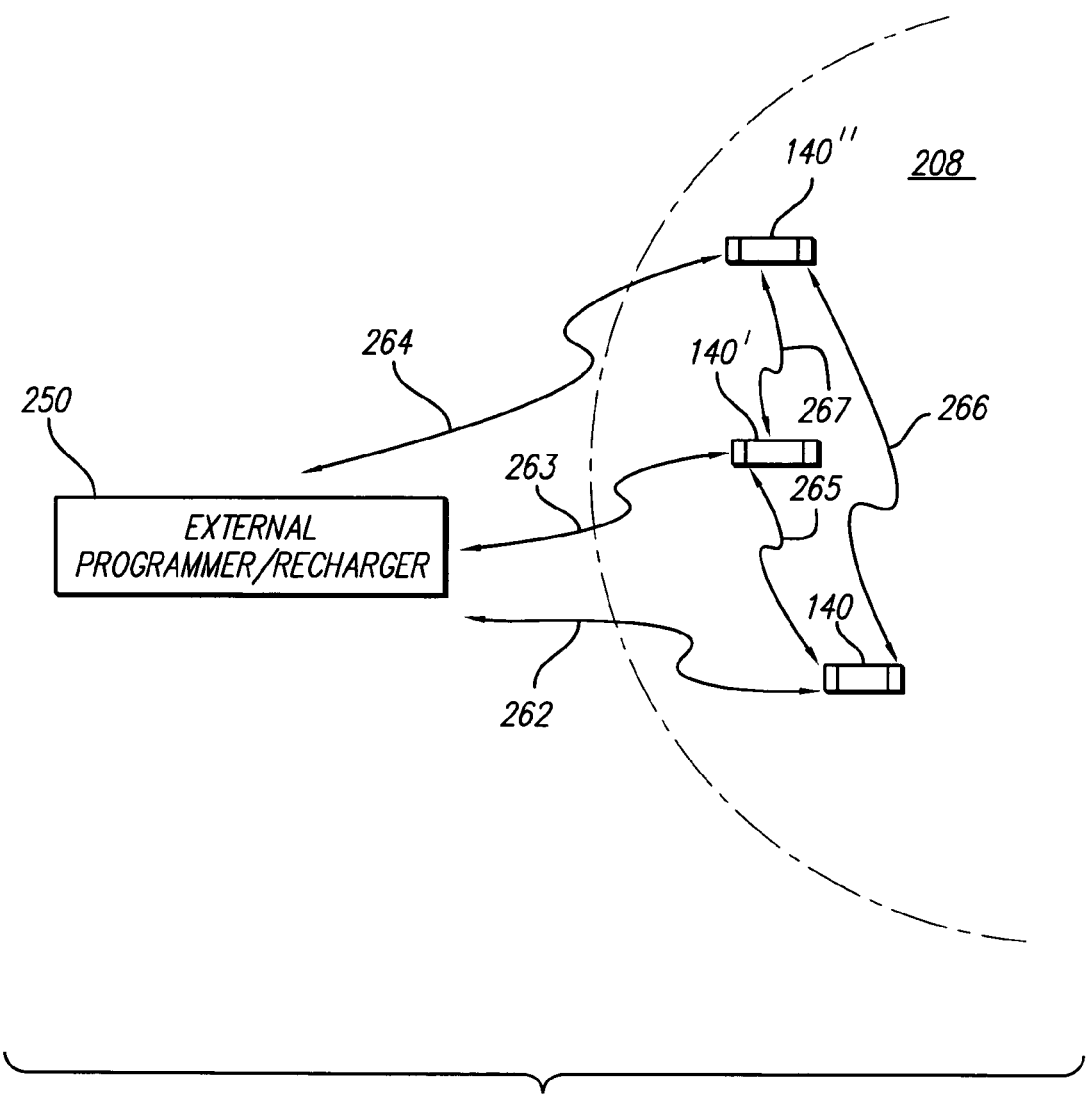
FIG. 4 depicts a number of stimulators configured to communicate with each other and/or with one or more external devices according to principles described herein.

A stimulator may be configured to operate independently. Alternatively, as shown in FIG. 4 and described in more detail below, the stimulator (140) may be configured to operate in a coordinated manner with one or more additional stimulators, other implanted devices, or other devices external to the patient's body. For instance, a first stimulator may control or operate under the control of a second stimulator, other implanted device, or other device external to the patient's body. The stimulator (140) may be configured to communicate with other implanted stimulators, other implanted devices, or other devices external to the patient's body via an RF link, an untrasonic link, an optical link, or any other type of communication link. For example, the stimulator (140) may be configured to communicate with an external remote control unit that is capable of sending commands and/or data to the stimulator (140) and that is configured to receive commands and/or data from the stimulator (140).

In order to determine the strength and/or duration of electrical stimulation and/or amount and/or type(s) of stimulating drug(s) required to most effectively treat obesity, various indicators of stomach activity, obesity, and/or a patient's response to treatment may be sensed or measured. These indicators include, but are not limited to, pressure against the stomach wall, stomach distension, stomach strain, naturally occurring electrical activity within the stomach (e.g., gastric slow waves), a rate of digestion of food within the stomach, and/or any other activity within the stomach. The indicators may additionally or alternatively include electrical activity of the brain (e.g., EEG); neurotransmitter levels; hormone levels; metabolic activity in the brain; blood flow rate in the head, neck or other areas of the body; medication levels within the patient; patient input, e.g., when a patient has the urge to eat, the patient can push a button on a remote control or other external unit to initiate the stimulation; temperature of tissue in the stimulation target region; physical activity level, e.g. based on accelerometer recordings; brain hyperexcitability, e.g. increased response of given tissue to the same input; indicators of collateral tissue stimulation; and/or detection of muscle tone (mechanical strain, pressure sensor, EMG). In some embodiments, the stimulator (140) may be configured to change the stimulation parameters in a closed loop manner in response to these measurements. The sensor (203; FIG. 2) within the stimulator (140; FIG. 2) may be configured to perform the measurements. Alternatively, other sensing devices may be configured to perform the measurements and transmit the measured values to the stimulator (140).

Thus, one or more external devices may be provided to interact with the stimulator (140), and may be used to accomplish at least one or more of the following functions:

Function 1: If necessary, transmit electrical power to the stimulator (140) in order to power the stimulator (140) and/or recharge the power source (145).

Function 2: Transmit data to the stimulator (140) in order to change the stimulation parameters used by the stimulator (140).

Function 3: Receive data indicating the state of the stimulator (140) (e.g., battery level, drug level, stimulation parameters, etc.).

Additional functions may include adjusting the stimulation parameters based on information sensed by the stimulator (140) or by other sensing devices.

By way of example, an exemplary method of treating a patient with obesity may be carried out according to the following sequence of procedures. The steps listed below may be modified, reordered, and/or added to as best serves a particular application.

1. A stimulator (140) is implanted so that its electrodes (142) and/or infusion outlet (149) are coupled to or located near the stomach.

2. The stimulator (140) is programmed to apply at least one stimulus to the stomach. The stimulus may include electrical stimulation, drug stimulation, chemical stimulation, thermal stimulation, electromagnetic stimulation, mechanical stimulation, and/or any other suitable stimulation.

3. When the patient desires to invoke stimulation, the patient sends a command to the stimulator (140) (e.g., via a remote control) such that the stimulator (140) delivers the prescribed stimulation. The stimulator (140) may be alternatively or additionally configured to automatically apply the stimulation in response to sensed indicators of stomach activity, digestion, or any other manifestation of obesity.

4. To cease stimulation, the patient may turn off the stimulator (140) (e.g., via a remote control).

5. Periodically, the power source (145) of the stimulator (140) is recharged, if necessary, in accordance with Function 1 described above. As will be described below, this recharging function can be made much more efficient using the principles disclosed herein.

In other examples, the treatment administered by the stimulator (140), i.e., drug therapy and/or electrical stimulation, may be automatic and not controlled or invoked by the patient.

For the treatment of different patients, it may be desirable to modify or adjust the algorithmic functions performed by the implanted and/or external components, as well as the surgical approaches. For example, in some situations, it may be desirable to employ more than one stimulator (140), each of which could be separately controlled by means of a digital address. Multiple channels and/or multiple patterns of stimulation may thereby be used to deal with various symptoms of obesity or various combinations of medical conditions.

As shown in the example of FIG. 4, a first stimulator (140) implanted within the patient (208) provides a stimulus to a first location; a second stimulator (140') provides a stimulus to a second location; and a third stimulator (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. stimulator (140), may control or operate under the control of another implanted device(s), e.g. stimulator (140') and/or stimulator (140"). Control lines (262-267) have been drawn in FIG. 4 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple stimulators (140) operating in a coordinated manner, the first and second stimulators (140, 140') of FIG. 4 may be configured to sense various indicators of stomach activity, digestion, or any other factor related to obesity and transmit the measured information to the third stimulator (140"). The third stimulator (140") may then use the measured information to adjust its stimulation parameters and apply stimulation to the stomach accordingly. The various implanted stimulators may, in any combination, sense indicators of stomach activity, digestion, or other factors related to obesity, communicate or receive data on such indicators, and adjust stimulation parameters accordingly.

Alternatively, the external device (250) or other external devices communicating with the external device (250) may be configured to sense various indicators of a patient's condition. The sensed indicators can then be collected by the external device (250) for relay to one or more of the implanted stimulators or may be transmitted directly to one or more of the implanted stimulators by any of an array of external sensing devices. In either case, the stimulator, upon receiving the sensed indicator(s), may adjust stimulation parameters accordingly. In other examples, the external controller (250) may determine whether any change to stimulation parameters is needed based on the sensed indicators. The external device (250) may then signal a command to one or more of the stimulators to adjust stimulation parameters accordingly.

Figure 5:
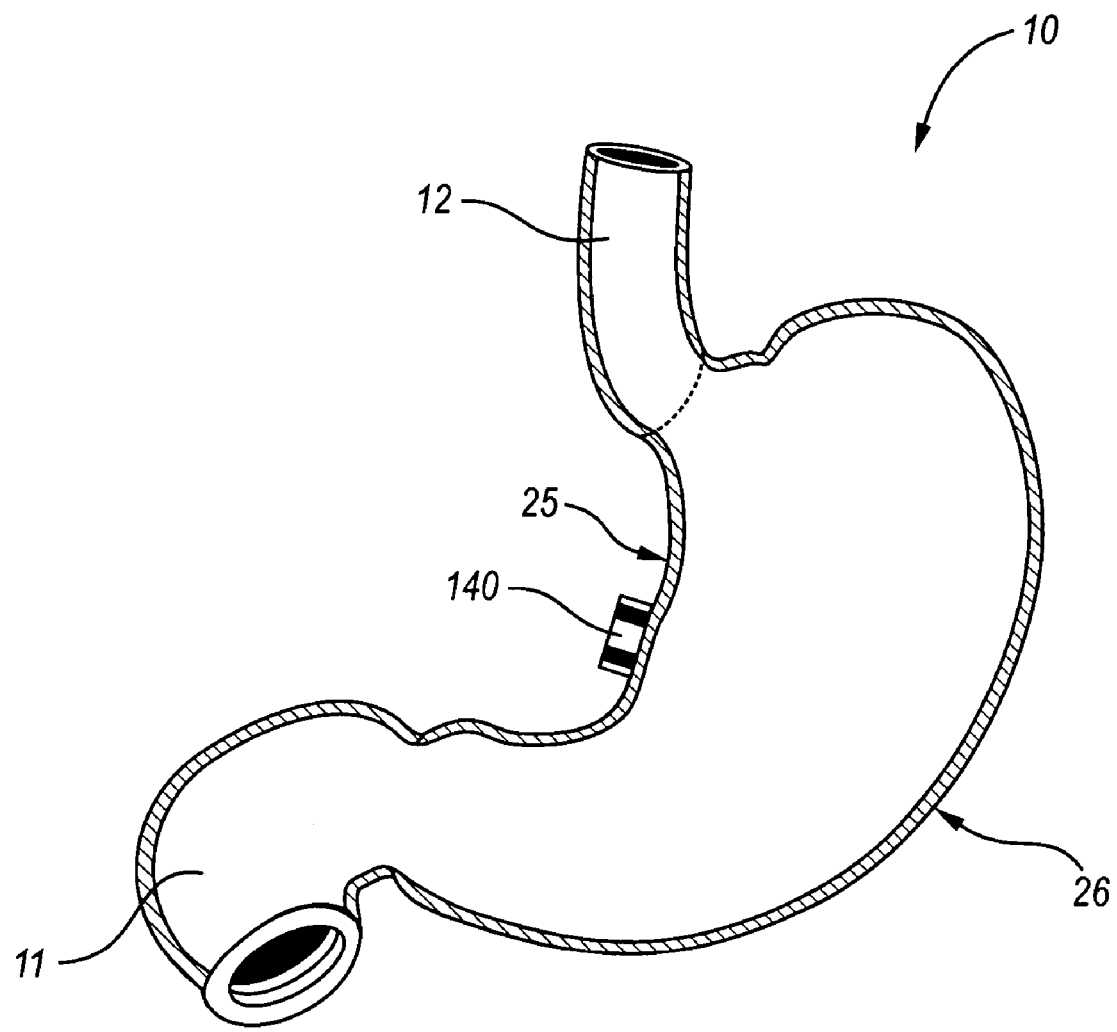
FIG. 5 illustrates an exemplary implanted stimulator that is coupled to the stomach according to principles described herein.

The stimulator (140) of FIG. 2 may be implanted within the patient using any suitable surgical procedure such as, but not limited to, injection, small incision, open placement, laparoscopy, or endoscopy. FIG. 5 illustrates an exemplary implanted stimulator (140) that is coupled to the stomach (10) to provide stimulation to the stomach (10). The stimulator is coupled to the lesser curvature (25) of the stomach (10) in FIG. 5 for illustrative purposes only. It will be recognized that the stimulator (140) may be coupled to any portion of the stomach (10) as best serves a particular application. For example, the stimulator (140) may be coupled to the greater curvature (26), cardia (20; FIG. 1A), fundus (21; FIG. 1A), antrum (23; FIG. 1A), pylorus (24; FIG. 1A), or any portion of the body (22; FIG. 1A) of the stomach (10). Additionally or alternatively, the stimulator (140) may be coupled to any of the five layers of the stomach (10), to a nerve that innervates the stomach (10), or to a blood vessel that supplies the stomach (10).

The stimulator (140) may be secured to the stomach (10) or to any other location within the body using any of a number of techniques. In some examples, the stimulator (140) is sutured to the stomach (10) using one or more sutures. Alternatively, a medical adhesive, hook, barb, or other securing device or material may be used to secure the stimulator (140) at a desired location.

Figure 6A:
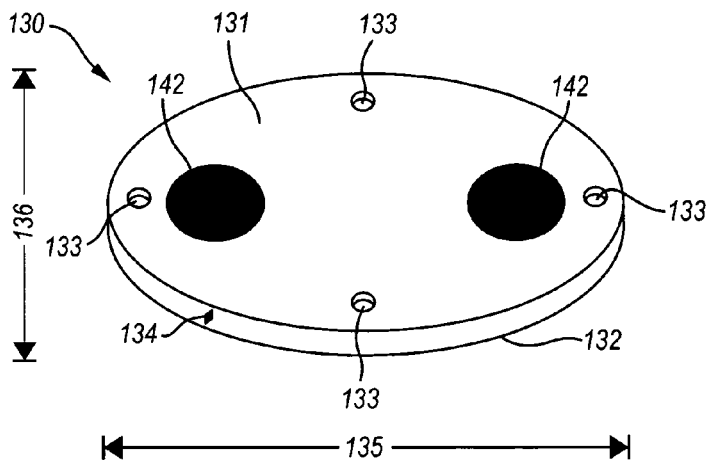
FIG. 6A is a perspective view of an exemplary insulative backing that may be used to couple the stimulator directly to the stomach according to principles described herein.

Alternatively, an affixation member, such as an insulative backing, may be used to couple the stimulator (140) directly to the wall of the stomach (10) or to any other structure in the body. FIG. 6A is a perspective view of an exemplary insulative backing (130) that may be used to couple the stimulator (140; FIG. 2) directly to the stomach. As shown in the example of FIG. 6A, the insulative backing (130) may be shaped like a flat, oval pad that includes a first surface (131) and a second surface (132) opposite the first surface (131). The first surface (131) is configured to be coupled to the stomach and the second surface (132) is configured to be coupled to the stimulator (140; FIG. 2).

The insulative backing (130) may be made out of any insulative material known in the art. For example, the insulative material may include, but is not limited to, silicone, ceramic, glass, or polyurethane. In some examples, the insulative backing (130) may be flexible so as to conform to the shape of the surface to which it is applied, for example, a curvature of the stomach.

As shown in FIG. 6A, the insulative backing (130) has a length (135), a width (136), and a thickness (134). It will be recognized that the length (135), width (136), and thickness (134) of the backing (130) may be any size as best serves a particular application. For example, in some embodiments, the length (135) is slightly longer than the length of the stimulator (140; FIG. 2) and the width (136) is approximately one half of an inch wide.

Furthermore, the insulative backing (130) may have any suitable shape as best serves a particular implantation site and/or particular type of stimulator. For example, the insulative backing (130) may have an oval-like shape, as shown in FIG. 6A. Alternatively, the insulative backing (130) may have a rectangular shape or any other suitable shape.

FIG. 6A shows that the insulative backing (130) may include a number of suture holes (133) so that the backing (130) may be sutured to the stomach. Four suture holes (133) are shown in FIG. 6A for illustrative purposes only. It will be recognized that the backing (130) may include any number of suture holes (133) arranged in any configuration as best serves a particular application.

Figure 6B:
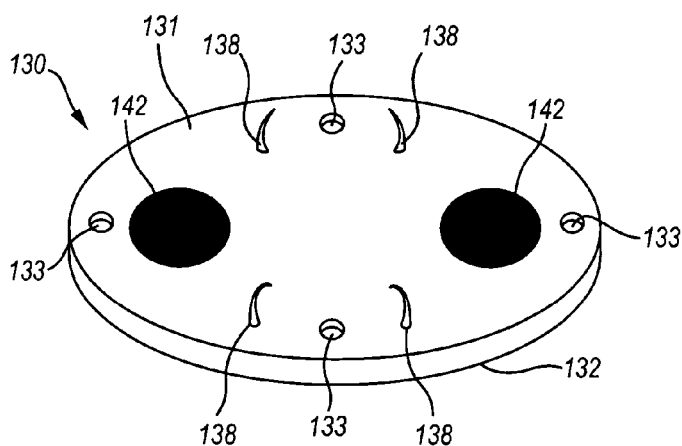
FIG. 6B is a perspective view of an exemplary insulative backing having a number of hooks configured to secure the backing to the stomach according to principles described herein.

Any other suitable securing device may be used to secure the backing (130) to the stomach. For example, as shown in FIG. 6B, a number of hooks or barbs may additionally or alternatively be included on the first surface (131) to secure the backing (130) to the stomach. A medical adhesive may also be used to secure the backing (130) to the stomach.

Thus, a variety of devices may be used to couple the first surface (131) of the backing (130) to the stomach. As indicated above, the stimulator (140; FIG. 2) is attached to the second surface (132) of the backing (130). The stimulator (140; FIG. 2) is then able to apply a stimulus to the stomach via the electrode contacts (142) disposed in the backing (130). Returning to FIG. 6A, a number of electrode contacts (142) are disposed on the first surface (131) of the insulative backing (130) through which an electrical stimulation current is applied to the stomach by the stimulator (140) coupled to the backing (130). In some examples, the insulative backing (130) includes two electrode contacts (142), as shown in FIG. 6A. However, any number of electrode contacts (142) may be disposed on the insulative backing (130) as best serves a particular application.

The electrode contacts (142) are oriented on one side of the insulative backing (130) so as to direct the stimulating current to the stomach. Hence, the insulative backing (130) and the electrode contacts (142) act as current field shaping instruments. In other words, the insulative backing (130) and/or the electrode contacts (142) disposed on the backing (130) force current to be directed towards the stomach and reduce useless and extraneous backwards current flow around portions of the stimulator (140). In some embodiments, the use of the insulative backing (130) may save up to forty percent or more of the total stimulation energy produced by the stimulator (140). Such energy efficiency increases battery life within the stimulator (140) and allows the stimulator (140) to have a smaller and more convenient size. Additionally, the added energy efficiency can reduce the amount of time the implant patient has to spend recharging the stimulator (140). Recharging the stimulator (140) may require that the patient limit mobility while energy is transferred to the stimulator (140) from an external charging device. The time during which recharging occurs and mobility is limited may consequently have a significant impact on the patient. Therefore, being able to limit the time spent recharging the stimulator (140) is of great potential value.

Figure 6C:
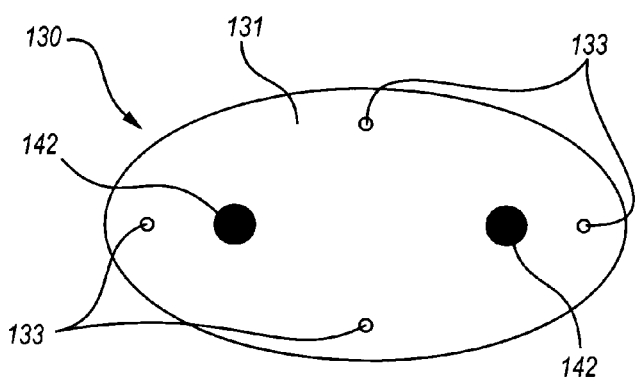
FIG. 6C is a top view of the insulative backing illustrated in FIG. 6A according to principles described herein.

FIGS. 6C is a top view of the insulative backing (130) shown in FIG. 6A. FIG. 6C shows the first surface (131) of the insulative backing (130) and shows the two electrode contacts (142) and four suture holes (133). The spacing between the electrode contacts (142) may vary as best serves a particular application.

As mentioned, any number of electrode contacts (142) may be disposed on the insulative backing (130). As will be explained in connection with FIGS. 7A-7H, the electrode contacts (152) may be arranged in an array with a variety of configurations to facilitate different types of stimulation or provide different current steering effects. Current steering is also known as neuronavigation or e-trolling. As used herein and in the appended claims, the term "current steering" will be used to describe a process used to determine the optimal stimulation parameters for a particular patient.

FIGS. 7A-7H illustrate a number of exemplary electrode contact arrangements that may be disposed on the first surface (131) of the insulative backing (130). As mentioned, the stimulator (140; FIG. 2) may be configured to provide monopolar and/or multipolar electrical stimulation. To this end, each electrode contact (142) may be selectively programmed or configured to act as an anode or as a cathode. Each electrode contact (142) may also be programmed to be "off," i.e., not part of the circuit delivering the stimulation current. Monopolar stimulation is achieved by using two electrode contacts of opposite polarity that are relatively far apart from each other. Bipolar stimulation is achieved by using two electrode contacts of opposite polarity that are relatively close to each other. Tripolar stimulation is achieved by using a cathode surrounded by two anodes or an anode surrounded by two cathodes.

Monopolar and multipolar electrode configurations often have different stimulation localization properties. For example, a monopolar electrode configuration emits a multi-directional electrical field that may be used to stimulate a relatively general stimulation site. A multipolar electrode configuration, on the other hand, emits a more localized electrical field that is often used to stimulate a relatively specific stimulation site, and may be used to stimulate stimulation sites that have a particular orientation (e.g., a nerve).

The electrode contacts (142) may be made of any conducting material that will withstand and operate effectively in an implanted environment. Such materials include, for example, a conducting ceramic, conducting polymer, copper, and/or a noble or refractory metal, such as gold, silver, platinum, iridium, tantalum, titanium, titanium nitride, niobium, and/or an alloy thereof. The use of one or more of these materials in constructing the electrode contacts (142) may serve to minimize corrosion, electrolysis, and/or damage to surrounding tissues.

The surfaces of the electrode contacts (142) may have any of a number of properties. For example, the surfaces may be smooth or rough. A rough surface increases the actual surface area of an electrode contact and may, with some materials (e.g., platinum or iridium), increase the pseudo-capacitance of the electrode contact. An increased pseudo-capacitance may serve to minimize the risk of adverse electrical affects to a patient being treated. A rough surface may also serve to help secure the adhesive backing (130) to the stomach.

Moreover, the electrode contacts (142) may have any size or shape that suits a particular application. Differently shaped electrode contacts (142) provide different current densities. For example, a round or oval electrode contact, as shown in FIGS. 7A-7H, may provide a more uniform current density than an electrode contact that is rectangular. However, the shape of the electrode contacts (142) may vary as best serves a particular application.

As mentioned, the electrode contacts (142) may be arranged in a variety of array configurations to facilitate different types of stimulation. FIGS. 7A-7H illustrate a number of exemplary electrode contact arrangements that may be used to provide monopolar and/or multipolar stimulation at the stomach. However, it will be recognized that the electrode contact arrangements shown in FIGS. 7A-7H are merely illustrative of the many different electrode contact arrangements that may be used to provide monopolar and/or multipolar stimulation at the stomach.

Figure 7A:
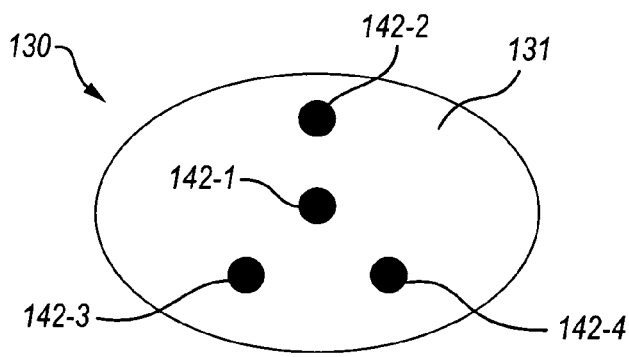
FIGS. 7A-7H illustrate a number of exemplary electrode contact arrangements that may be disposed on the first surface of the insulative backing according to principles described herein.

For example, FIG. 7A shows a first electrode contact arrangement that may be used to provide monopolar and/or multipolar stimulation at the stomach. The electrode contact arrangement of FIG. 7A includes a center electrode contact (142-1) surrounded by three electrode contacts (142-2,3,4) in an equilateral triangle or trigonal planar configuration. As mentioned, each of the electrode contacts (142) may be selectively configured to act as an anode or cathode. Hence, monopolar stimulation may be achieved by using, for example, the top electrode contact (142-2) and one of the bottom electrode contacts (e.g., 142-3) as an anode-cathode pair. Bipolar stimulation may be achieved by using, for example, the center electrode contact (142-1) with one of the other electrode contacts (e.g., 142-2) as an anode-cathode pair. Tripolar stimulation may be achieved by using, for example, the center electrode contacts (142-1) with two of the other electrode contacts (e.g., 142-3 and 142-4) in an anode-cathode-anode or cathode-anode-cathode configuration.

Figure 7B:
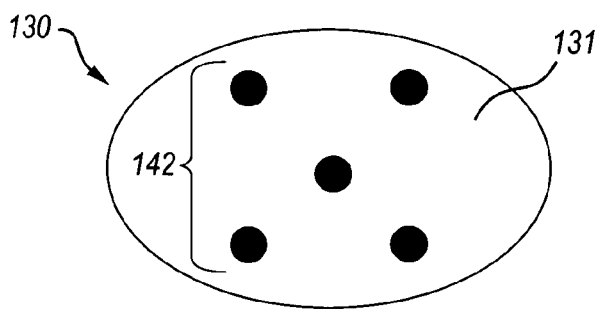
Figure 7C:
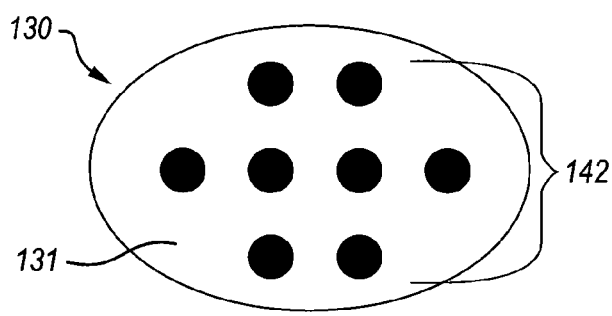
Figure 7D:
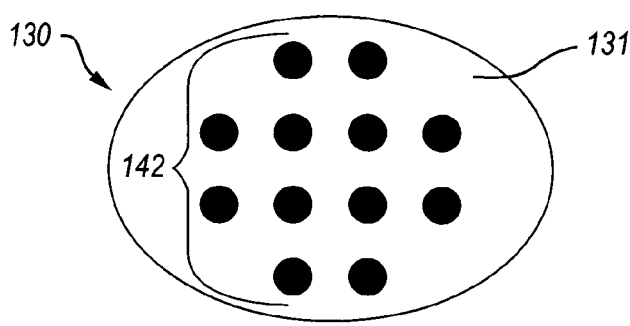

As illustrated in FIGS. 7A-7H, there are many possible configurations for the electrode contact array. The illustrated examples are merely exemplary and other configurations are within the scope of the principles described herein. FIG. 7B illustrates a configuration with a central electrode contact (142) and four additional electrode contacts (142) arranged in a square around the central electrode contact (142). FIG. 7C illustrated a line of four electrode contacts (142) with a line of two electrode contacts (142) both above and below the line of four, with the lines of two electrode contacts (142) each being centered with respect to the larger line of four. FIG. 7D illustrates a similar configuration only with two lines of four electrode contacts (142) arranged between the upper and lower lines of two.

Figure 7E:
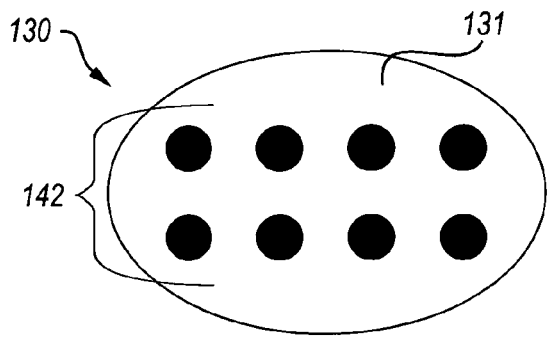
Figure 7F:
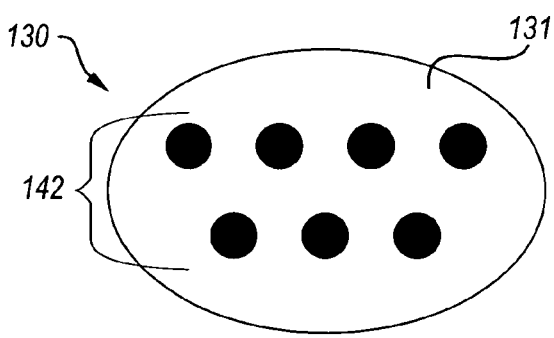
Figure 7G:
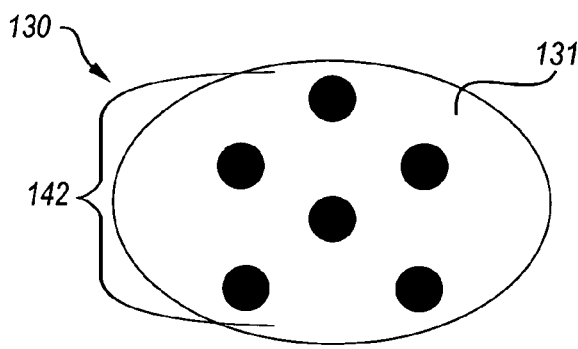
Figure 7H:
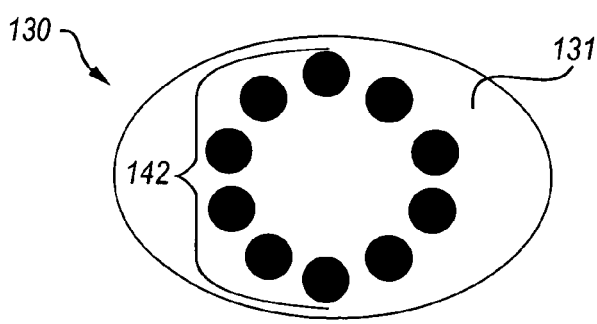

FIG. 7E illustrates a configuration in which the electrode contacts (142) are arranged in a two-by-four rectangular array. FIG. 7F illustrates a configuration in which a line of four electrode contacts (142) is disposed adjacent a line of three electrodes. FIG. 7G illustrated a configuration with six electrode contacts (142) in three columns of two electrode contacts (142) each. The center column is offset vertically with respect to the two side columns. FIG. 7H illustrates a configuration in which the electrode contacts (142) are arranged in a circle or ring pattern. Each configuration illustrated and other possible configurations for the electrode contacts (142) will provide different current steering options and may be particularly well suited for treating obesity in a particular patient.

Figure 8:
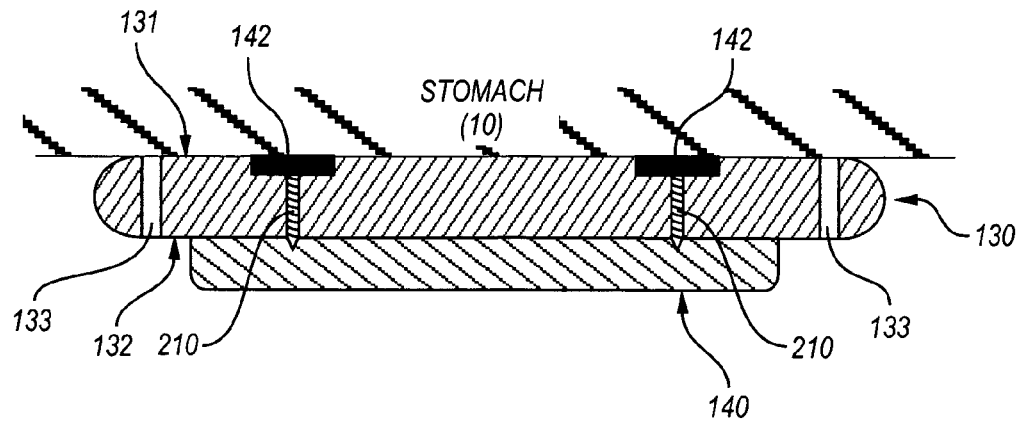
FIG. 8 is a cross-sectional side view of an insulative backing and stimulator coupled to the stomach according to principles described herein.

FIG. 8 is a cross-sectional side view of an insulative backing (130) and stimulator (140) coupled to the stomach (10). As shown in FIG. 8, the first surface (131) of the insulative backing (130) is coupled to the stomach (10) and the second surface (132) of the insulative backing (130) is coupled to the stimulator (140). Alternatively, the stimulator (140) may be integrated with the insulative backing (130) so as to be at least partially enclosed in the insulative backing (130). One side of the insulative backing (130) would still provide a first surface (131) having two or more electrode contacts (142) disposed thereon.

As shown in FIG. 8, the electrode contacts (142) are electrically and/or magnetically coupled to the implanted stimulator (140). For example, one or more conductive vias (210) may be used to electrically couple the electrode contacts (142) to the electrical circuitry (144; FIG. 2) of the implanted stimulator (140). The conductive vias (210) may include conductive wires, metal traces, or any other material configured to electrically couple the electrode contacts (142) to the stimulator (140). Thus coupled, electrical stimulation generated by the stimulator (140) may be applied to the stomach (10) via the electrode contacts (142).

Returning to FIG. 5, the stimulator (140) is configured to apply stimulation to the stomach (10) based on the measurements of the sensor (203; FIG. 2). In some examples, the sensor (203; FIG. 2) is configured to sense stomach distension that occurs as food enters the stomach (10). The sensor (203; FIG. 2) may additionally or alternatively be configured to sense electrical activity (e.g., gastric slow waves) of the stomach (10) or any other stomach or related activity as described above.

In some examples, the stimulator (140) enables or turns on the stimulation to the stomach (10) when the sensor (203; FIG. 2) senses one or more indicators of stomach activity, digestion, or other factors related to obesity. For example, the stimulator (140) may be configured to enable stimulation of the stomach (10) when the sensor (203; FIG. 2) senses stomach distension or electrical activity produced by the stomach (10).

The various stimulation parameters (e.g., frequency, pulse width, amplitude, electrode polarity configuration, burst pattern, duty cycle, ramp on time, and ramp off time) associated with the stimulation may be continuously adjusted in response to the sensed obesity factors. In some examples, the stimulation parameters are automatically adjusted by the stimulator (140) in response to the sensed obesity factors. For example, the stimulator (140) may automatically increase the frequency and/or amplitude of the stimulation if the sensor (203; FIG. 2) senses an increase in stomach distension or electrical activity produced by the stomach (10). The stimulation causes the patient to feel a sensation of fullness before the stomach (10) fully distends such that the patient eats less.

The stimulator (140) may additionally or alternatively be configured to stimulate the stomach (10) during periods of time during which the patient is not eating so that the patient feels a sensation of fullness, thereby reducing the patient's desire to eat. The frequency of stimulation may be programmed and adjusted as best serves a particular patient.

In some examples, the stimulator (140) is configured to provide intermittent stimulation to the stomach (10). Intermittent stimulation is also referred to as demand pacing stimulation. In intermittent stimulation, the stimulator (140) is configured to intermittently disable or turn off the stimulation to the stomach (10). Intermittent stimulation increases the effectiveness of the stimulation for some obese patients by preventing the stomach (10) and/or neurological system of the patient from adapting to the stimulation. Intermittent stimulation is also beneficial in many applications because it requires less battery power than does continuous stimulation. Hence, the stimulator (140) may operate longer without being recharged, the power source (145; FIG. 2) may be smaller, and the overall size of the stimulator (140) may be reduced.

Figure 9:
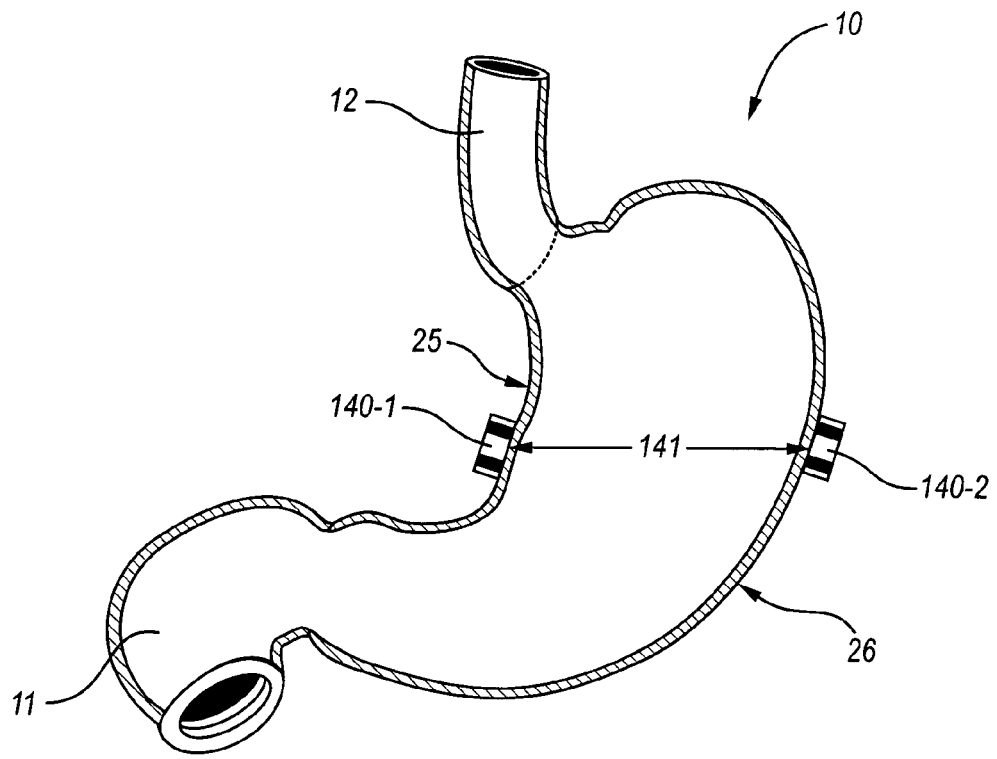
FIG. 9 illustrates an exemplary configuration wherein multiple stimulators are coupled to the stomach according to principles described herein.

FIG. 9 illustrates an exemplary configuration wherein multiple stimulators (140-1, 140-2) are coupled to the stomach (10) to provide stimulation to the stomach (10). FIG. 9 shows a first stimulator (140-1) coupled to the lesser curvature (25) of the stomach (10) and a second stimulator (140-1) coupled to the greater curvature (26) of the stomach (10). However, it will be recognized that any number of stimulators (140) may be coupled to any portion of the stomach (10) as best serves a particular application.

In some examples, stomach distension may be sensed by measuring the distance between two stimulators (140) that are coupled to the stomach (10). For example, the separation distance (141) between the stimulators (140-1, 140-2) of FIG. 9 may be measured to sense stomach distension. As the stomach (10) distends due to the intake of food, the separation distance (141) increases. One or more of the stimulators (140-1, 140-2) may then turn on, adjust, or turn off stimulation to the stomach (10) in response to this change in separation distance (141) between the stimulators (140-1, 140-2).

In some embodiments, the stimulators (140-1, 140-2) are configured to sense the separation distance (141) by communicating with each other using one or more RF fields. For example, the first stimulator (140-1) may be configured to transmit an RF field and the second stimulator (140-2) may be configured to sense the signal strength of the RF field transmitted by the first stimulator (140-1). When the stomach (10) distends due to an intake of food, the separation distance (141) between the two stimulators (140-1, 140-2) increases, thereby decreasing the sensed signal strength of the transmitted RF field. The second stimulator (140-2) senses this decrease in signal strength of the RF field transmitted by the first stimulator (140-1). One or more of the stimulators (140-

1, 140-2) may then stimulate the stomach (10) in response to this decrease in sensed signal strength of the transmitted RF field. The stimulation applied may be proportional to the decrease in signal strength of the transmitted RF field allowing for a continuum of possible stimulation levels dictated by the amount of stomach distention. It will be recognized that the first and second stimulators (140-1, 140-2) may communicate via any suitable communication link including, but not limited to, an infrared (IR) link, an optical link, or Bluetooth™.

Figure 10:
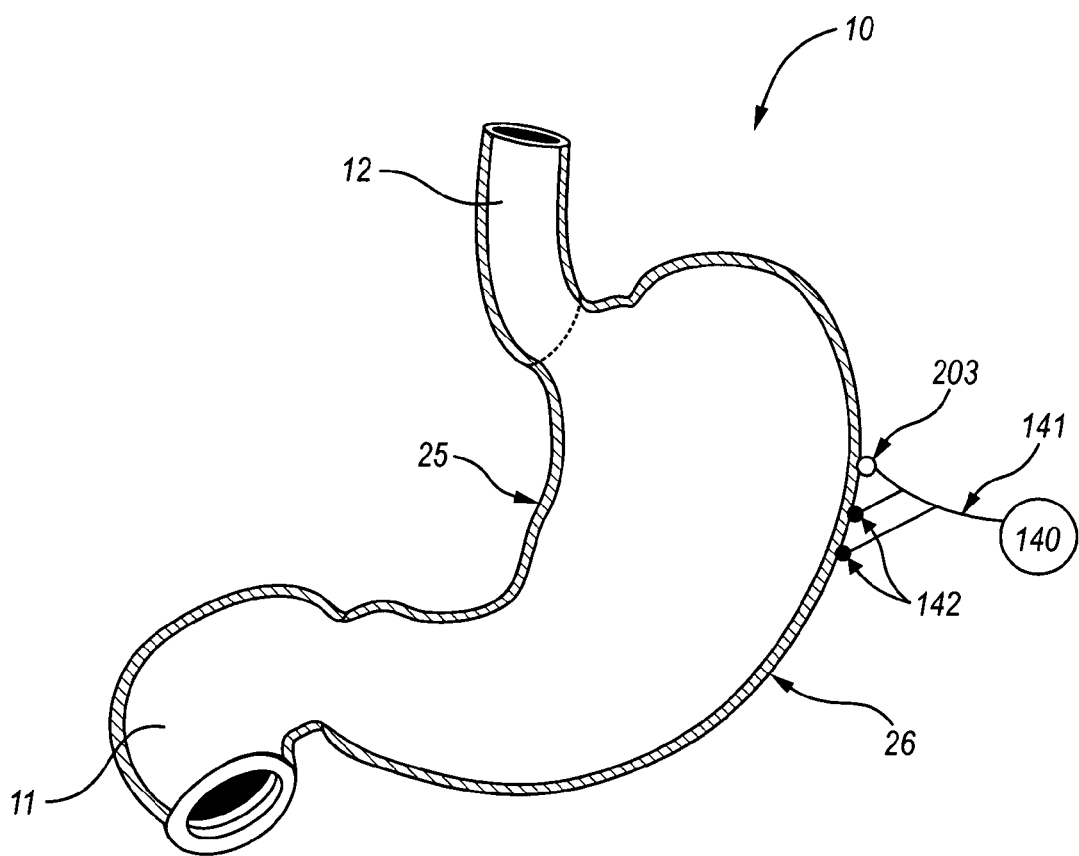
FIG. 10 illustrates an exemplary configuration wherein a stimulator is configured to stimulate the stomach via a number of electrodes disposed on a lead according to principles described herein.

FIG. 10 illustrates an exemplary configuration wherein a stimulator (140) is configured to stimulate the stomach (10) via a number of electrodes (142) disposed on a lead (141). As shown in FIG. 10, the stimulator (140) may be implanted in any convenient location in the patient, e.g., in the abdominal wall. The lead (141) extends away from the stimulator (140) towards the stomach (10) such that its electrode contacts (141) touch or are in close proximity to the stomach (10). In some embodiments, the lead (141) may additionally be coupled to a sensor (203) that is also located at or near the stomach (10). A catheter (143; FIG. 2) may additionally or alternatively be coupled to the stimulator (140) and configured to apply one or more drugs to the stomach.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system for treating an obese patient, said system comprising:
    a first stimulator configured to be coupled to a first location of a stomach of said patient; and
    a second stimulator configured to be coupled to a second location of said stomach of said patient;
    wherein at least one of said first and second stimulators is further configured to sense distension of said stomach by sensing a separation distance between said first and second stimulators; and
    wherein said at least one of said first and second stimulators is further configured to apply a stimulus to said stomach of said patient in response to said sensed distension of said stomach.

2. The system of claim 1, wherein said first and second locations of said stomach comprise at least one or more of a lesser curvature of said stomach, a greater curvature of said stomach, a wall of said stomach, a cardia of said stomach, a fundus of said stomach, an antrum of said stomach, a pylorus of said stomach, a layer of said stomach, a nerve that innervates said stomach, and a blood vessel that supplies said stomach.

3. The system of claim 1, further comprising:
    one or more electrode contacts electrically coupled to at least one of said first and second stimulators;
    wherein said stimulus comprises an electrical stimulation current delivered to said stomach via said electrode contacts.

4. The system of claim 1, wherein said stimulus comprises one or more drugs delivered at said stomach.

5. The system of claim 1, wherein said stimulus comprises an intermittent stimulation.

6. The system of claim 1, wherein said first and second stimulators are coupled directly to a wall of said stomach.

7. The system of claim 1, wherein:
    said first stimulator is configured to emit a signal having a signal strength;
    said second stimulator is configured to sense said signal strength; and
    wherein at least one of said first and second stimulators is configured to determine said separation distance based on said sensed signal strength.

8. The system of claim 7, wherein said second stimulator is configured to sense a change in said signal strength, said change in signal strength corresponding to a change in said distension of said stomach, and wherein said at least one of said first and second stimulators is configured to adjust said stimulus in response to said change in said distension of said stomach.

9. A method of treating an obese patient, said method comprising:
    coupling a first stimulator to a first location of a stomach of said patient;
    coupling a second stimulator to a second location of the stomach of said patient;
    sensing a separation distance between said first and second stimulators to determine a distension of said stomach; and
    applying a stimulus to said stomach of said patient in response to said sensed distension of said stomach.

10. The method of claim 9, wherein said first and second locations of said stomach comprise at least one or more of a lesser curvature of said stomach, a greater curvature of said stomach, a wall of said stomach, a cardia of said stomach, a fundus of said stomach, an antrum of said stomach, a pylorus of said stomach, a layer of said stomach, a nerve that innervates said stomach, and a blood vessel that supplies said stomach.

11. The method of claim 9, wherein said stimulus comprises an electrical stimulation current delivered to said stomach.

12. The method of claim 9, wherein said stimulus comprises one or more drugs delivered at said stomach.

13. The method of claim 9, wherein said step of applying said stimulus to said stomach comprises intermittently stimulating said stomach in response to said sensed distension of said stomach.

14. The method of claim 9, further comprising coupling a body of at least one of said first and second stimulators directly to a wall of said stomach.

15. The method of claim 9, further comprising:
    emitting a signal having a signal strength with said first stimulator;
    sensing said signal strength with said second stimulator; and
    determining said separation distance based on said sensed signal strength.

16. The method of claim 9, further comprising:
    sensing a change in said signal strength, said change in signal strength corresponding to a change in said distension of said stomach; and
    adjusting said stimulus in response to said change in said distension of said stomach.

17. A method comprising:
    coupling a first stimulator to a first location of a stomach of said patient;
    coupling a second stimulator to a second location of the stomach of said patient;
    emitting a signal having a signal strength with said first stimulator;
    sensing said signal strength with said second stimulator;
    determining a separation distance based on said sensed signal strength; and
    applying a stimulus to said stomach of said patient in accordance with said sensed signal strength.

* * * * *